United States Patent [19]

Ferdinandi et al.

[11] Patent Number: 4,994,381
[45] Date of Patent: Feb. 19, 1991

[54] N-[[6-METHOXY-5-(TRIFLUOROMETHYL)-1-NAPHTHALENYL]-THIOXOMETHYL]-N-METHYLGLYCINE S-OXIDE AND THE AMIDE THEREOF

[75] Inventors: Eckhardt S. Ferdinandi, Princeton; Michael S. Malamas, Plainsboro; Kazimir Sestanj, Monmouth Junction; Surendra N. Sehgal, Princeton, all of N.J.

[73] Assignee: American Home Products Corporation, New York, N.Y.

[21] Appl. No.: 325,605

[22] Filed: Mar. 20, 1989

Related U.S. Application Data

[62] Division of Ser. No. 113,691, Oct. 28, 1987, Pat. No. 4,853,484, which is a division of Ser. No. 934,760, Nov. 25, 1986, Pat. No. 4,734,435, which in turn is a continuation-in-part of Ser. No. 849,242, Jul. 7, 1986, abandoned.

[51] Int. Cl.⁵ .................. C12P 13/04; C12P 11/00; C12P 13/02
[52] U.S. Cl. .................. 435/106; 435/129; 435/130; 435/897
[58] Field of Search .......... 435/106, 116, 130, 897, 435/129

[56] References Cited

U.S. PATENT DOCUMENTS

| | | | |
|---|---|---|---|
| 3,821,383 | 6/1974 | Sestanj et al. | 514/296 |
| 4,157,278 | 6/1979 | Ross et al. | 435/272 |
| 4,254,108 | 3/1981 | Sestanj | 514/296 X |
| 4,254,109 | 3/1981 | Sestanj | 514/296 X |
| 4,317,779 | 3/1982 | Crawford | 260/400 |
| 4,369,188 | 1/1983 | Sestanj | 514/411 |
| 4,391,816 | 7/1983 | Sestanj et al. | 514/562 X |
| 4,391,825 | 7/1983 | Bellini et al. | 514/562 |
| 4,439,617 | 3/1984 | Sestanj | 560/39 |
| 4,447,452 | 5/1984 | Sestanj | 514/567 |
| 4,672,058 | 6/1987 | Bellini et al. | 514/563 X |
| 4,734,435 | 3/1988 | Ferdinandi et al. | 514/562 |
| 4,853,484 | 8/1989 | Ferdinandi et al. | 564/74 |

FOREIGN PATENT DOCUMENTS 45-12318  5/1970  Japan .................. 564/74

OTHER PUBLICATIONS

Walter, Justus Liebigs Ann. Chem., pp. 1584–1597 (1976).

Primary Examiner—Carolyn S. Elmore
Attorney, Agent, or Firm—Walter Patton

[57] ABSTRACT

Disclosed herein are N-[[6-methoxy-5-(trifluoromethyl)-1-naphthalenyl]-thioxmethyl]-N-methylglycine S-oxide (tolrestat S-oxide) and the amine thereof and methods of their preparation. The S-oxides are new aldose reductase inhibitors useful for the treatment or prevention of diabetic complications.

1 Claim, No Drawings

N-[[6-METHOXY-5-(TRIFLUOROMETHYL)-1-NAPHTHALENYL]-THIOXOMETHYL]-N-METHYLGLYCINE S-OXIDE AND THE AMIDE THEREOF

This is a divisional application of co-pending application Ser. No. 07/113,691 filed on Oct. 28, 1987 issued as U.S. Pat. No. 4,853,484 on Aug. 1, 1989, which in turn is a divisional application of co-pending application Ser. No. 06/934,760 filed on Nov. 25, 1986 issued as U.S. Pat. No. 4,734,435 on Mar. 29, 1988, which in turn is a continuation-in-part application of co-pending application Ser. No. 06/849,242 filed July 7, 1986, now abandoned.

BACKGROUND OF THE INVENTION

This invention relates to N-[[6-methoxy-5-(trifluoromethyl)-1-naphthalenyl]thioxomethyl]-N-methylglycine S-oxide and the amide thereof, to processes for their preparation, to methods for using the derivatives, and to pharmaceutical preparations thereof. The derivatives have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem. Biophys. Acta, 158,472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

1,3-Dioxo-1H-benz[de]isoquinoline-2(3H)-acetic acid has been reported to be an effective inhibitor of aldose reductase, see D. Dvornik et al, Science, 182,1146 (1973), and to be useful for the treatment of diabetic complications such as diabetic cataracts, neuropathy, nephropathy and retinopathy, see K. Sestanj, N. Simard-Duquesne and D. Dvornik, U.S. Pat. No. 3,821,383, June 28, 1974. Other compounds having a similar utility are the thioxo-1H-benz[de]isoquinoline-2(3H)-acetic acid derivatives of K. Sestanj, U.S. Pat. No. 4,254,108, Mar. 3, 1981 and 1H-benz[de]isoquinoline-2(3H)-acetic acid derivatives of K. Sestanj, U.S. Pat. No. 4,254,109, Mar. 3, 1981. Still other compounds having a similar utility are 2-thioxobenz[c,d]indole-1(2H)-acetic acid derivatives of K. Sestanj, U.S. Pat. No. 4,369,188, Jan. 18, 1983; N-naphthoylglycine derivatives of K. Sestanj et al, U.S. Pat. No. 4,439,617, Mar. 27, 1984; N-(naphthalenylthioxomethyl)amino acid derivatives of K. Sestanj et al, U.S. Pat. No. 4,391,816, July 5, 1983; N-[2-naphthalenyl)thioxomethyl]glycine derivatives of K. Sestanj, U.S. Pat. No. 4,447,452, May 8, 1984; and N-[[6-(lower alkoxy)-5-(trifluoromethylthio)-1-naphthalenyl]thioxomethyl]-N-(lower alkyl)-glycines of F. Bellini et al, U.S. Pat. No. 4,391,825, July 5, 1983. Accordingly, these compounds represent an important new approach for the treatment of diabetes mellitus.

The present application discloses the novel N-[[6-methoxy-5-(trifluoromethyl)-1-naphthalenyl]thioxomethyl]-N-methylglycine S-oxide and the amide thereof represented below by formula I, which are effective inhibitors of aldose reductase. They are structurally different from the above noted aldose reductase inhibitors. The closest of the previously reported compounds are seen in U.S. Pat. No. 4,439,617 (Example 52), and U.S. Ser. No. 743,336, filed June 10, 1985. The present derivatives differ by being S-oxides.

SUMMARY OF THE INVENTION

The N-[[6-methoxy-5-(trifluoromethyl)-1-naphthalenyl]thioxomethyl]-N-methylglycine S-oxide and the amide thereof of this invention are represented by formula I

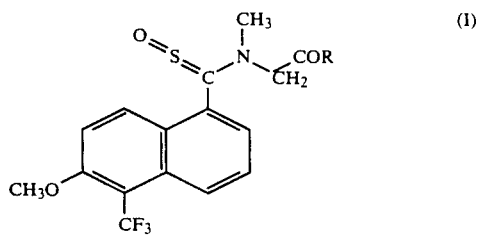

wherein R is —OH or —NH$_2$ and the pharmaceutically acceptable salts thereof.

The N-[[6-methoxy-5-(trifluoromethyl)-1-naphthalenyl]thioxomethyl]-N-methylglycin S-oxide and the amide thereof can be prepared by the processes described hereinafter.

A method is provided for preventing or relieving diabetes mellitus associated complications in a diabetic mammal by administering to said mammal a prophylactic or alleviating amount of a compound of formula I. Such complications include neuropathy, nephropathy, retinopathy and cataracts.

The compounds of formula I, when admixed with a pharmaceutically acceptable carrier, forms a pharmaceutical composition which can be used according to the preceding method.

DETAILED DESCRIPTION OF THE INVENTION

The compounds of this invention, represented by formula I, can exist in rotameric forms. More explicitly, mesomerism imparts a partial double bond character to the carbon-nitrogen bond of the thioamide S-oxide group. This partial double bond character leads to restricted rotation about the carbon nitrogen bond giving rise to cis and trans rotamers, the restricted rotation being augmented by the bulkiness of neighboring groups. The rotameteric forms are included within the scope of this invention. For brevity, the compounds of this invention, including their rotameric forms, are referred to herein as compounds of formula I.

The N-[[6-methoxy-5-(trifluoromethyl)-1-naphthalenyl]thioxomethyl]-N-methylglycine S-oxide and the amide thereof of this invention may be adminstered to mammals, for example, man, monkeys or dogs, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6, containing a pharmaceutically acceptable buffer.

The dosage of the N-[[6-methoxy-5-(trifluoromethyl)-1-naphthalenyl]thioxomethyl]-N-methylglycine S-oxide and the amide thereof will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05-1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N-[[6-methoxy-5-(trifluoromethyl)-1-naphthalenyl]thioxomethyl]-N-methylglycine S-oxide and the amide thereof can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the N-[[6-methoxy-5-(trifluoromethyl)-1-naphthalenyl]thioxomethyl]-N-methylglycin S-oxide and the amide thereof are administered as described previously. The N-[[6-methoxy-5-(trifluoromethyl)-1-naphthalenyl]thioxomethyl]-N-methylglycine S-oxide and the amide thereof can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications are demonstrable in experiments using galactosemic rats, see Dvornik et al, cited above. Such experiments are exemplified hereinbelow after the listing of the following general comments pertaining to these experiments:

(a) Four or more groups of six male rats, 50-70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the N-[[6-methoxy-5-(trifluoromethyl)-1-naphthalenyl]thioxomethyl]-N-methylglycine S-oxide and the amide thereof of this invention show the property that they diminish the accumulation of galactitol in the lenses and sciatic nerves of rats fed galactose. The figures under L and N represent the percentage decrease of galactitol accumulation in the tissues of the lens and sciatic nerve, respectively, for treated rats as compared to untreated rats.

Examination of the results tabulated below show that the N-[[6-methoxy-5-(trifluoromethyl)-1-naphthalenyl]-thioxomethyl]-N-methylglycine S-oxide and the amide thereof of this invention are well suited as aldose reductase inhibitors. For example, N-[[6-methoxy-5-(trifluoromethyl)-1-naphthalenyl]thioxomethyl]-N-methylglycine S-oxide at a dose of 50 mg/kg/day and [[[6-methoxy-5-(trifluoromethyl)-1-naphthalenyl]thioximethyl]methylamino]-acetamide S-oxide at a dose of 58 mg/kg/day give comparable results to N-[[6-methoxy-5-(trifluoromethyl)-1-naphthalenyl]-thioxomethyl]-N-methylglycine at 10 mg/kg/day. The latter compound, is also known as tolrestat.

A compound of this invention [(I), R= —OH] is one of the metabolites of tolrestat found in humans and other mammals.

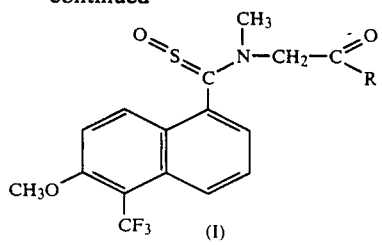

wherein R is as defined above. For example, N-[[6-methoxy-5-(trifluoromethyl)-1-naphthalenyl]thioxomethyl]-N-methylglycine [tolrestat, (II, R=—OH)] is oxidized with an oxidizing agent such as, hydrogen peroxide, in a buffered solution with cooling to produce (I), R=—OH. The pH of the buffer is preferably acidic.

Specifically, tolrestat oxidized with hydrogen peroxide in methylene chloride at a pH of about 4 with cooling to about 0° C. produces the desired S-oxide (I), R=—OH.

Tolrestat amide [(II), R= —NH$_2$] is oxidized with m-chloroperbenzoic acid (m-CPBA) in methylene chloride to produce (I), R= —NH$_2$.

The compound of the present invention [(I), R=

| Test compound | % inhibition in vitro 10-7 M | mg/kg/day | % lowering dulcitol accumulation in vivo L | N | Mode of administration |
|---|---|---|---|---|---|
| N-[[6-methoxy-5-(trifluoromethyl)-1-naphthalenyl]thioxomethyl]-N-methylglycine S-oxide | 80 | 115 | 20 | 100 | diet |
| N-[[6-methoxy-5-(trifluoromethyl)-1-naphthalenyl]thioxomethyl]-N-methylglycine S-oxide | 80 | 20 | 0 | 45 | diet |
| N-[[6-methoxy-5-(trifluoromethyl)-1-naphthalenyl]thioxomethyl]-N-methylglycine S-oxide | 80 | 50 | 0 | 70 | gavage* |
| [[[6-methoxy-5-(trifluoromethyl)-1-naphthalnyl]thioxomethyl]methyl-amino]-acetamide S-oxide | 3 | 58 | 0 | 77 | |
| [[[6-methoxy-5-(trifluoromethyl)-1-naphthalenyl]thioxomethyl]methyl-amino]-acetamide S-oxide | 3 | 12 | 0 | 45 | |
| N-[[6-methoxy-5-(trifluoromethyl)-1-naphthalenyl]carbonyl]-N-methylglycine | 60 | 50 | 0 | 59 | gavage* |
| N-[[6-methoxy-5-(trifluoromethyl)-1-naphthalenyl]thioxomethyl]-N-methylglycine (tolrestat) | 65 | 10 | 0 | 81 | gavage* |

*Data involving gavage administration were obtained in the same experiment.

THE PROCESS

The N-[[6-methoxy-5-(trifluoromethyl)-1-naphthalenyl]thioxomethyl]-N-methylglycine S-oxide and the amide thereof can be prepared by the following reaction scheme:

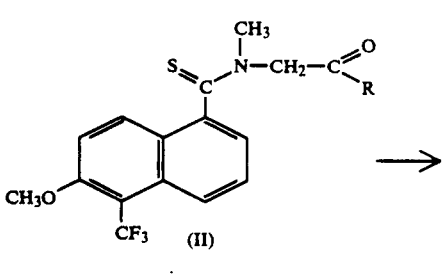

—OH] was also produced by microbial fermentation.

The following Examples further illustrate this invention.

EXAMPLE 1

N-[[6-Methoxy-5-(trifluoromethyl)-1-naphthalenyl]thioxomethyl]-N-methylglycine S-oxide

[(I), R= OH]

To a 0° C. solution of N-[[6-methoxy-5-(trifluoromethyl)-1-naphthalenyl]thioxomethyl]-N-methylglycine, (tolrestat) (2.0 g, 5.6 mmol, prepared by the procedure of U.S. Pat. No. 4,439,617) in CH$_2$Cl$_2$ (100 mL) was added potassium phthalate buffer pH=4 (20 mL), followed after 10 minutes by H$_2$O$_2$ (30%, 30 mL).

After stirring vigorously for 24 hours, the mixture was cooled to −20° C. for 30 minutes and the precipitated solid was filtered and recrystallized from acetone/H₂O (at 0° C.) to yield a white solid, m.p. 156°–157° C. (1.8 g, 86.1%).

IR (KBr, cm⁻¹): 2800–2200 (br), 1750 (s), 1610 (s), 1530 (s), 1510 (s), 1080 (s), 880 (s).

NMR (DMSO—d₆, 200 MHz) δ 2.67 (s, 3H, N—CH₃), 4.07 (s, 3H, —OCH₃), 4.7 (d, Jab=17.2 Hz, 1H), 5.95 (d, Jab=17.2 Hz, 1H), 7.46 (d, J=6.6 Hz, 1H, ArH), 7.7 (dd, J=9.0 Hz, 1H, ArH), 7.79 (d, J=9/0 Hz, 1H, Ar-H), 8.24 (m, 1H, ArH), 8.76 (d, J=9.6 Hz, 1H, Ar-H).

MS: (m/e) 373 (M+), 357 (M+—O), 253 (M+—S, -sarcosine).

Anal. Calcd: C, 51.50; H, 3.78; N, 3.75%. Found: C, 51.20; H, 3.71; N, 3.74%.

EXAMPLE 2

Production of N-[[6-Methoxy-5-(trifluoromethyl)-1-naphthalenyl]thioxomethyl]-N-methylglycine S-oxide by Fermentation.

[(I), R= —OH]

*Streptomyces griseus* ATCC 12475 was grown in a soybean meal-glucose medium. After 48 hours 0.5 mg/mL of N-[[6-methoxy-5-(trifluoromethyl)-1-naphthalenyl]thioxomethyl]-N-methylglycine [tolrestat, (II)], dissolved in a minimal amount of methanol, was charged into the growth medium with stirring and incubation continued for 72 hours at 28° C. At the end of incubation the fermentation broth was extracted with methylene chloride. The organic solvent was evaporated to dryness. N-[[6-Methoxy-5-(trifluoromethyl)-1-naphthalenyl]thioxomethyl]-N-methylglycine S-oxide was isolated and purified by thick layer chromatography.

EXAMPLE 3

[[[6-Methoxy-5-(trifluoromethyl)-1-naphthalenyl]thioxomethyl]methylamino]-acetamide S-oxide

[(I), R= —NH₂]

To a −78° C. solution of [[[6-methoxy-5-(trifluoromethyl)-1-naphthalenyl]thioxomethyl]methylamino]acetamide (prepared by the process of U.S. Ser. No. 743,336, filed June 10, 1985) (5.0 g, 14.04 mmol) in anhydrous CH₂Cl₂ (200 mL) was added m-CPBA (2.42 g, 14.04 mmol) portionwise over a 10 minute period. After stirring for 2 hours at −78° C., the mixture was poured into a −78° C. solution of hexane (500 mL) and the precipitated solid was filtered and recrystallized from acetone/H₂O (at 0° C.) to yield a yellow solid (3.65 g, 70%) of m.p. 194°–195° C.

NMR (DMSO-d₆, 400 MHz): δ 2.61 (s, N—CH₃, 3H), 4.04 (s, AR—OCH₃ 3H), 4.4 (d, J=16.2 Hz, —NCHCONH₂, 1H), 6.1 (d, J=16.2 Hz, —NCHCONH₂, 1H), 7.23 (s, —CONH, 1H), 7.45 (d, J=6.9 Hz, 1H, Ar—H), 7.66 (m, Ar—H, —CONH, 2H), 7.75 (d, J=9.6 Hz, 1H, Ar—H), 8.2 (d, J=8.6 Hz, 1H, Ar—H), 9.0 (d, J=9.5 Hz, 1H, Ar—H)

M/S: (m/e) 373 (M+H)⁺, 357 (M+H—O), 340 (M+H—SH), 323 (M+H—SH, —NH₃)

Anal. Calcd: C, 51.61; H, 4.06; N, 7.52%. Found: C, 51.60; H, 3.90; N, 7.40%.

We claim:

1. A process for preparing the compound N-[[6-methoxy-5-(trifluoromethyl)-1-naphthalenyl]thioxomethyl]-N-methylglycine S-oxide, which comprises fermentation of *Streptomyces griseus* ATCC 12475 in the presence of N-[[6-methoxy-5-(trifluoromethyl)-1-naphthalenyl]thioxomethyl]-N-methylglycine and isolation of said S-oxide compound.

* * * * *